US005120322A

United States Patent [19]

Davis et al.

[11] Patent Number: 5,120,322

[45] Date of Patent: Jun. 9, 1992

[54] METHOD AND APPARATUS FOR TREATMENT OF FIBROTIC LESIONS

[75] Inventors: William M. Davis; Milos Chvapil, both of Tucson, Ariz.

[73] Assignee: Lathrotec, Inc., Tucson, Ariz.

[21] Appl. No.: 538,025

[22] Filed: Jun. 13, 1990

[51] Int. Cl.[5] ........................ A61M 5/32; A61M 25/00

[52] U.S. Cl. ........................................ 604/265; 604/49; 128/898; 514/526; 424/447

[58] Field of Search ........................ 514/526, 660, 665; 424/447; 128/898; 604/265, 46-49, 51-53

[56] References Cited

U.S. PATENT DOCUMENTS 4,444,787 4/1984 Moorhead ........................... 514/526
4,485,088 11/1984 Chvapil ............................... 424/447
4,997,854 3/1991 Kagan et al. ........................ 514/660
5,021,404 6/1991 Folkman et al. ...................... 514/26
5,043,441 8/1991 Peck et al. .......................... 540/526

OTHER PUBLICATIONS

Chem. Abst. 78, 24,205(g) (1973)-Bora et al.
Chem. Abst. 95, 54,914 (1981)-Moorehead.
Chem. Abst. 103, 594(s) (1985)-Speer et al.

*Primary Examiner*—C. Fred Rosenbaum
*Assistant Examiner*—Mark O. Polutta
*Attorney, Agent, or Firm*—Austin R. Miller

[57] ABSTRACT

A method of controlling scar formation in humans by applying a force to tissue in an amount to create a wound;
applying a lathyrogenic agent to the wound;
forming the wound into a predetermined stationary or moveable beneficial configuration; and
maintaining the wound in the predetermined configuration and in contact with lathyrogenic agent during healing.

28 Claims, 2 Drawing Sheets

14 20 26 22 26 20 14 10

METHOD AND APPARATUS FOR TREATMENT OF FIBROTIC LESIONS

FIELD OF THE INVENTION

This invention relates to a novel method and apparatus for treating fibrotic lesions, particularly to treating scar tissue wherever located, and to treating strictures of tubular structures, hollow organs and the like.

1. Background of the Invention

Whether created by disease, accident or therapeutic intervention, mammals heal their wounds by formation of scar tissue. The healing process, namely scar formation, often leaves mammals with limitations of motion, constricting skin scars, frozen joints or restriction of organ function such as in urethral stenosis or gastric outlet obstruction, for example.

For many years, medical practitioners and researchers have struggled unsuccessfully with the difficult task of controlling scar formation by either reducing scar production or promoting scar resorption in their efforts to reduce limitations of motion, scarring, freezing of joints or restriction of organ function. Their efforts prior to this time have not been successful in alleviating these problems in human patients.

2. Description of the Prior Art

During the past quarter century much knowledge has been gained relative to the biochemistry of scar formation. E.E. Peacock, Jr. & Walton VanWinkle in *Wound Repair.* Sanders Company, Philadelphia, USA, 1976, among others, have reported their work in this regard. In simple terms, scar is a woven protein consisting primarily of special amino acid strands of fibers called collagen. Collagen is formed in special wound cells (fibroblast) which is extruded to mature in an extracellular matrix where eventual strength is obtained by crosslinking of protein collagen fibers. The cross-linking process, which gives scar its strength and hardness, is facilitated by the enzyme lysyl oxidase.

U.S. Pat. No. 4,485,088 to Chvapil discloses that crosslinking can be inhibited by altering several chemical pathways with compounds called lathyrogens, such as D-Penicillamine and Beta-aninopropionitrile (BAPN). These compounds have been administered systemically to insure their incorporation into the healing process. Unfortunately, their therapeutic and toxic concentrations are so close that they cannot be systemically tolerated by humans, thereby precluding their application to human patients.

The therapeutic effects of inhibiting or modifying collagen crosslinking has been demonstrated with topical application to healing wound scars by Chvapil. One of the lathyrogens, BAPN, penetrates the skin and other surrounding tissues a few millimeters in thickness. The effective dose of topical BAPN has been reported to be approximately 1/100th the systemically effective dose, thereby reducing in importance, but not eliminating, the issue of safety. Chvapil describes topical application to burn scars, skin and chicken tendons at or near the time of injury and new scar formation. However, Chvapil's technique is limited to topical applications or applications where the lathyrogens may be injected into a localized area, such as a joint or tendon.

Similar experimental work has been performed for treatment of dogs with regard to burns in the esophagus; Davis et al in "A New Approach to the Control of Esophageal Stenosis", *Ann. Surg.*, Vol. 176, No. 4 (October 1972). However, serious toxicity problems were encountered with systemically introduced Beta-aminopropionitrile fumarate (BAPN-F). Moreover, during the treatment time, the subjects exhibited severe problems in the ingestion of food.

Madden et al reported in "Experimental Esophageal Lye Burns", *Ann. Surc.*, Vol. 178, No. 3 (September 1973), that although they believed that mechanical splints should be applied continuously for many months to achieve permanent correction in artificially induced esophaeal burns, bougienage could only be performed intermittently.

OBJECTS OF THE INVENTION

It is accordingly an object of this invention to provide a method of treatment of fibrotic lesions to reduce limitations of motion, scarring, freezing of joints or restriction of organ function, all without encountering problems as to systemic toleration.

A further object is to provide novel equipment for carrying the method into effect.

SUMMARY OF THE INVENTION

This invention relates to a novel method of controlling scar formation in a manner which preserves organ functions by the combination of biochemistry, pharmacology and physics by (1) forceful resection or dilation of a scarred area in a human patient to create a new wound, followed by (2) continuous topical application of a lathyrogenic agent to the dilated scarred area and (3) during healing of the new wound continuously supporting the dilated scarred area in the desired configuration.

The invention further relates to a special catheter for controlling scar formation, onto which a selected lathyrogen may be bonded prior to insertion into generally tubular portions of the human or animal body, followed by rehealing while supporting the tubular body portion in the desired configuration.

DETAILED DESCRIPTION OF THE INVENTION

Figure 1:
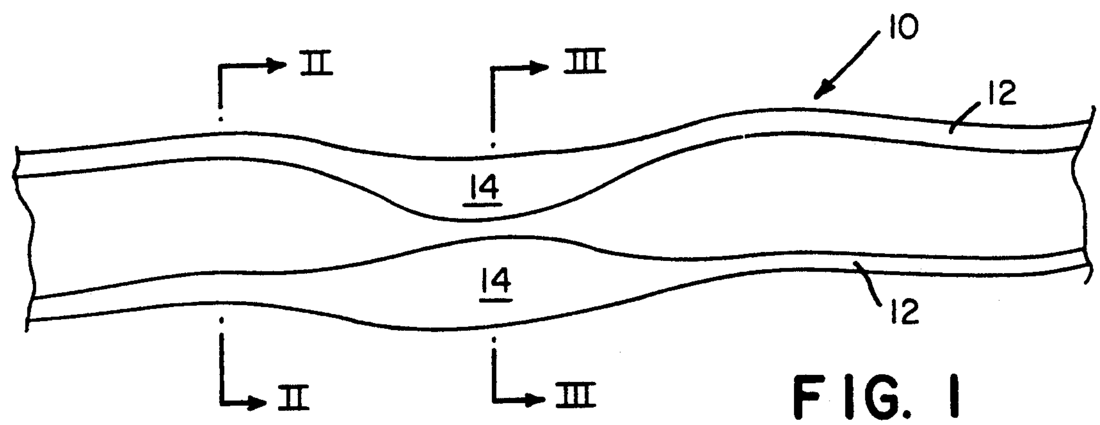
FIG. 1 shows a schematic front elevational view taken in section, of a tubular organ exhibiting severe stenosis.

Although a particular form of apparatus and method has been selected for illustration in the drawings, and although specific terms will be used in the specification for the sake of clarity in describing the apparatus and method shown, the scope of this invention is defined in the appended claims and is not intended to be limited either by the drawings selected or the terms used in the specification or abstract. For example, although fibrotic lesion on hollow organs have been illustrated in the drawings for convenience, the method of the invention is not intended to be limited to such hollow organs.

As shown in FIG. 1, which is a schematic of a tubular organ 10, a portion of the tissue 12 exhibits severe stenosis. The portion exhibiting such stenosis is designated by the numeral 14.

The stenotic portion 14 may be the result of any number of naturally occurring or artificially induced occurrences. For example, portion 14 may have been previously injured, such as by surgical operation, severe injury, trauma or the like. Stenotic portion 14 resulted from the formation of scar tissue, which grew into and toward the center portion of tubular organ 10. The result of the formation of such scar tissue is the severe narrowing of tubular organ 10.

Narrowing of tubular organ 10 can have severe consequences with regard to the passage of fluids through the tube. For example, in the case where tubular organ 10 represents the urethral canal, almost complete blockage of flow can occur. This, of course, is highly undesirable. The same severe consequences may result in instances where tubular organ 10 represents the esophagus, blood vessels, intestinal passageways, fallopian tubes and the like.

Figure 2:
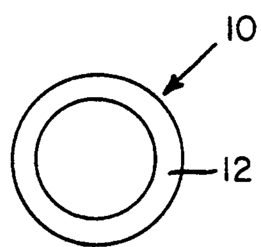
FIG. 2 shows a section of the tubular organ taken along the lines and arrows II of FIG. 1.
Figure 3:
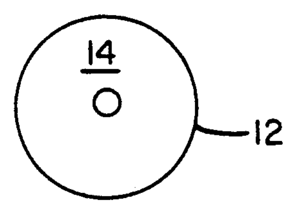
FIG. 3 shows a section of the tubular organ taken along the lines and arrows III of FIG. 1.

FIG. 2 of the drawings shows a portion of tubular organ 10 which is in a normal, non-stenotic condition. Tissue 12 is of ordinary thickness. On the other hand, FIG. 3 shows a stenotic portion 14 of tubular organ 10 wherein tissue 12 has a far greater thickness, and reduces the interior diameter of the tube.

Figure 4:
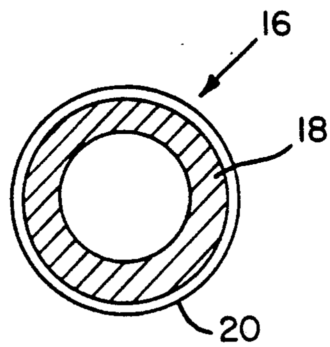
FIG. 4 is a schematic sectional view of a catheter having a lathyrogenic agent applied thereto.
Figure 5:
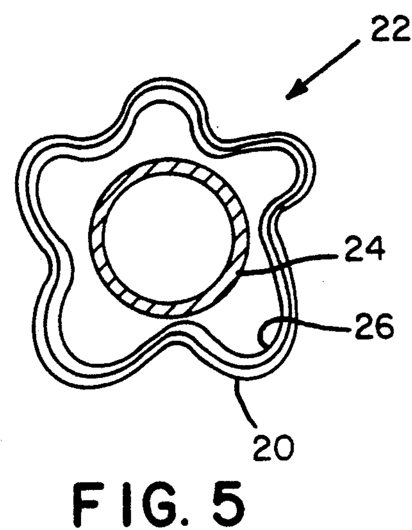
FIG. 5 is a schematic sectional view of a balloon catheter having a lathyrogenic agent applied thereto.

Referring now to FIGS. 4 and 5, different forms of catheters are shown. FIG. 4 illustrates a simple tubular catheter 16. Tubular catheter 16 includes a hollow tube 18 surrounded by lathyrogenic agent 20. Similarly, FIG. 5 shows balloon catheter 22. .Balloon catheter 22 consists of a central tube 24 and a balloon 26. Balloon 26 is coated with and is surrounded by lathyrogenic agent 20.

Figure 6:
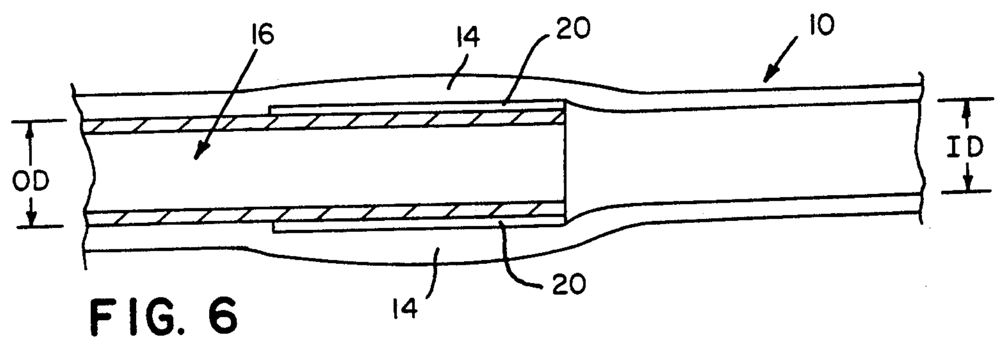
FIG. 6 is a schematic view, taken in section, of a catheter inserted in a tubular organ in accordance with aspects of the invention.

FIG. 6 schematically illustrates insertion of one form of tubular catheter 16 into tubular organ 10. Tubular catheter 16, as shown, has an outer diameter OD which is greater than the inner diameter ID of tubular organ 10. Tubular catheter 16 extends into tubular organ 10 for a distance sufficient to engage stenotic portion 14. Tubular catheter 16 is inserted to a point wherein lathyrogenic agent 20 directly and closely contacts substantially all of stenotic portion 14.

Figure 7:
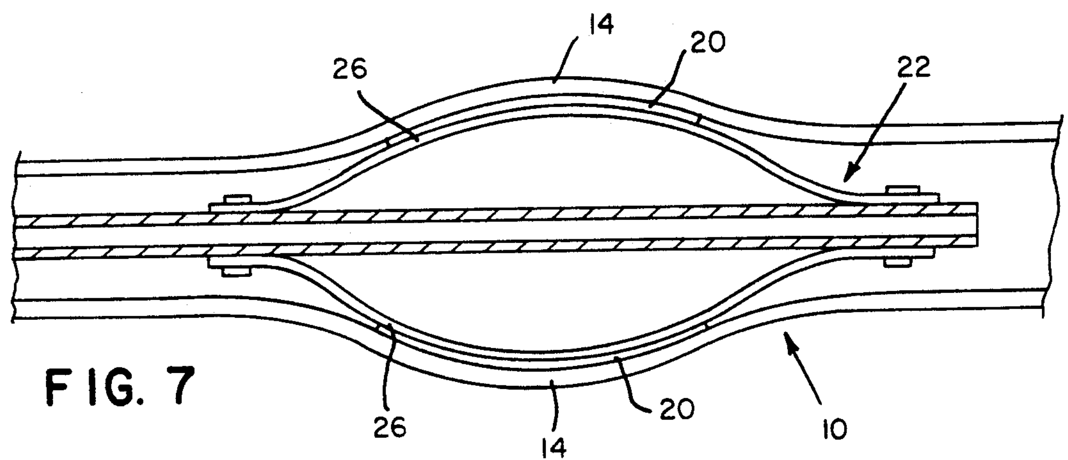
FIG. 7 is a schematic view, taken in section, of a balloon catheter inserted in a tubular organ in accordance with aspects of the invention.

FIG. 7 shows balloon catheter 22 in an inflated condition within tubular organ 10. Balloon catheter 22 extends inwardly into tubular organ 10 to a point wherein lathyrogenic agent 20, which surrounds balloon 26, directly and closely contacts stenotic portion 14.

Figure 8:
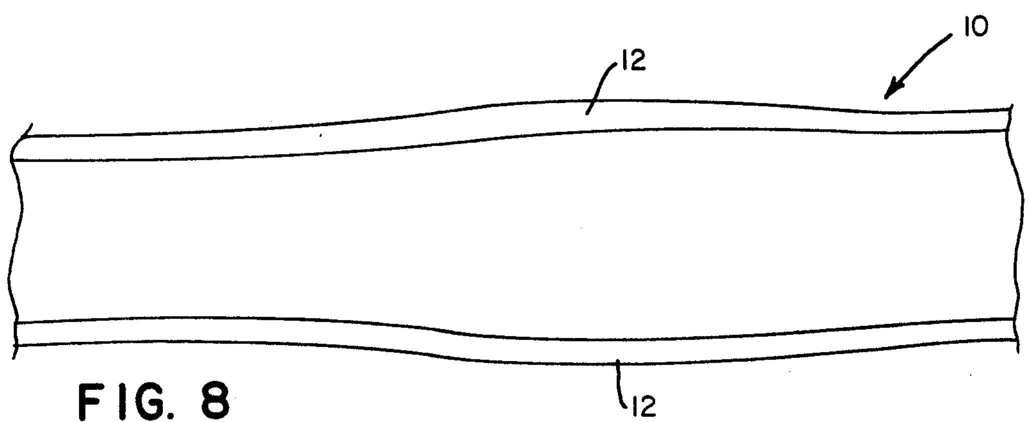
FIG. 8 shows a schematic view, taken in section, of a tubular organ after treatment in accordance with the method of the invention.

FIG. 8 shows tubular organ 10 after removal of either tubular catheter 16 or balloon catheter 22. Tissue 12 is in a normal condition and thickness throughout the entire length of tubular organ 10. Stenotic portion 14 is no longer present.

In accordance with a preferred form of the invention, the physician locates a stenotic portion of the tubular organ by ordinary means well known in the art. Once the stenotic portion has been identified and located, it is dilated, resected, incised or removed to create a fresh, open wound. Then a lathyrogenic agent, preferably D-penicillinamine or Beta-aminopropionitrile (BAPN), or Beta-aminopropionitrile fumarate (BAPN-F), or aminoacetonitrile, for example, is applied to a catheter of the physician's choice. Depending upon the tubular organ to which the catheter is applied, various well known catheters may be utilized. In the case where a balloon catheter is chosen, the lathyrogenic agent (sometimes referred to hereinafter for convenience as BAPN-F) is applied in a coating to the balloon portion of the catheter, such as shown in FIG. 5 of the drawings.

The catheter is then inserted into the tubular organ by ordinary means well known in the art. The balloon catheter is inserted to a point where the BAPN is in position to directly and closely contact stenotic portion 14 upon expansion of the balloon. The balloon is then inflated and left in position for the prescribed treatment time.

It has been discovered that the lathyrogenic agent should be applied to target tissue in a dose of about 4.5 mM to about 8.5 mM for BAPN-F and about 20 mM to about 40 mM for D-penicillamine. The preferred dose is between about 5.0 mM and about 5.5 mM for BAPN-F and about 22mM to about 25 mM for D-penicillamine.

In another preferred form of the invention, the BAPN-F is ionically bonded to a special catheter capable of ionically bonding the BAPN-F to the cuter surface of the catheter. This ionic bonding permits insertion of the catheter within the tube and up to the stenotic portion, without the danger of BAPN-F being wiped off the catheter prior to contact with the stenotic portion. In this manner, the coated catheter is inserted after the stenotic portion has been expanded or resected to a degree which tears or removes the existing scar tissue. The BAPN-F then directly contacts the tissue in the new wound to soften the healing process. The resulting formed tissue is substantially in the shape and size of the outer diameter of the catheter and retains its normal pliant condition, and exhibits the characteristics of normal, uninjured tissue.

In still another preferred form of the invention, the same steps may be applied to non-tubular tissue. For example, the method of the invention may be applied to exterior burns such as skin burns. However, it is important that the same steps be followed to achieve the excellent results achievable with this aspect of the invention. Examples of various applications of the method of the invention are illustrated as follows:

EXAMPLE 1 —BURN SCAR-ELBOW

A patient with a full thickness dermal scar around the elbow, exhibits complete contracture and cannot fully extend the elbow. This restricts use. The hard scar is surgically "released" under general anesthesia by cutting in several places with or without a skin graft. The patient then has a lathyrogen applied and is placed in an elbow dynamic splint. This allows the elbow to be protected and at the same time to fully exercise the joint on a daily basis with or without the supervision of a physical therapist.

A lathyrogen jelly with 5.0 mM of BAPN-F and/or 20–25 mM D-penicillamine or a BAPN-F ]impregnated gauze (40 mg/100 cm$^2$ of gauze) is continuously applied to the wound during its healing phase beginning 4–8 days after surgical treatment and continued for four to six weeks in combination with physical therapy. At the end of healing, the splint is removed, the lathyrogen discontinued and the patient resumes full range of motion at the elbow due to the lack of cross-linking of newly formed collagen in place of old scar tissue.

EXAMPLE 2 —FALLOPIAN TUBE STENOSIS-INFERTILITY

A patient having scarred and blocked fallopian tubes as a result of infection has incisions made in the scar tissue and a BAPN- coated silastic tube stint placed in the fallopian tube after one week and left in place during the healing phase. The stint is continuously maintained in contact with the fresh wound and is changed two or three times during the four to six week healing phase as the lathyrogenic agent leaches off the surface of the silastic stint and is incorporated into the newly healing scar. The newly formed scar takes the shape of the stint. The stint is removed, the opening of the fallopian tube is preserved and egg and sperm transport can now cross the previously blocked fallopian tube.

EXAMPLE 3 —ESOPHAGEAL STRUCTURE

A young teenager, who as a child swallowed a drain cleaning solution, has a lye burn to the lower esophagus and has great difficulty with maintaining proper nutrition. The result is stunted growth. The scar formed from the burn is dilated under direct endoscopic vision with a dilator or surgically resected to create fresh wound tissue. A Cellestin tube is immediately attached across the new wound area and continuously maintained in position for the duration of healing. The outer lining of the Cellestin tube consists of silicone to which a combination of D-Penicillamine and BAPN-F is bonded, which leaches into the healing area. When healing is complete the tube is removed and a normal esophageal diameter remains because the 5.0 mM solutions of the lathyrogens have been incorporated into the new scar allowing it to form itself around the tube without further stenosis.

EXAMPLE 4 —URETHRA-PROSTATIC CANCER

A patient with prostatic cancer detected with sonography and a candidate for total prostatectomy has the prostate removed and the cuff of the bladder sewn to the most proximal remaining portion of the urethra. This circumferential suture line often progresses to heavy scarring preventing complete emptying of the bladder. The scar is cut away under anesthesia and direct resectoscope vision and immediately stinted with a silicone catheter coated with 5.0 mM BAPN-F. The catheter remains in continuous direct contact with the new wound tissue during healing. The BAPN-F leaches from the surface of the catheter, thereby inhibiting hardening of the healing scar during the next three weeks. The catheter is changed on a weekly basis to renew the BAPN-F supply. Once healing is complete and the newly formed scar is laid down around the stint of the indwelling bladder urethra catheter, no new scarring takes place.

EXAMPLE 5 —BURN SCAR-HAND

A patient with a well healed full thickness burn of the hand has severe scarring of the fingers and hand in a claw-like form. The old scars are surgically released to create full mobility of the joints. The hand is placed in a "dynamic splint." The splint contains rubber band fixation to a rigid frame allowing the patient to exercise his fingers through a full range of motion. During the healing phase and on a daily basis, a jelly containing 5 mM/L of the lathyrogenic agent BAPN-F is continuously applied to the surgically "released" areas. The patient continues to exercise and use the dynamic splint during the healing phase over the next four to six weeks. Once re-epithelialization and healing is complete, the newly formed scar, being softened by the continuous application of BAPN-F, has full range of motion without further restriction of hand motion. The dynamic splint is removed. Healing is complete and range of motion restored.

EXAMPLE 6 —BURN SCAR-NECK

A patient with severe third degree burn of the neck has completed healing, but the resulting scar is so severe that the head cannot be straightened. The sca is surgically released (incised) with or without a skin graft, thereby creating a new wound. A stiff plastic collar having a soft lining is applied to the neck to hold it in a new desired position. A combination of 5.0 mM BAPN-F and 20-25 D-Penicillinamine jelly or a BAPN-F impregnated gauze (40 mg/100 $cm^2$ of gauze) is continuously applied to the newly created wound tissue so that as new scar is formed, it will be soft, plastic-like, and uncross-linked until healing is complete in four to six weeks. A the end of that time no new medication need be applied, the collar is removed and the patient has been restored to full range of motion of the neck.

EXAMPLE 7 —URETHRA-INFECTION

A patient with urethral stenosis (narrowing of the tube between the bladder and the end of the penis) secondary to a gonococcal infection exhibits bladder outlet obstruction. The old scar in the urethra is opened under direct surgical resection. Immediately afterward a silicone urethral bladder catheter is inserted. After one week, this catheter is exchanged for one with the lathyrogenic agent BAPN-F bonded onto its surface. The coated catheter is continuously maintained in place and changed ever week for about six weeks during the healing phase. During the healing phase new scar tissue is laid down. However, its strength is beneficially altered by the lathyrogen BAPN-F which inhibits the bonding of one protein scar fiber to the next protein scar fiber allowing the wound to be molded in the shape of the intraluminal stint (urinary bladder catheter). At the end of the healing phase, the stint is removed and normal unobstructed urination can proceed.

EXAMPLE 8 —URETHRA-TRAUMA

Following fractured hips, 5-10% of human males suffer transection of the membranous urethra as it leaves the bladder. This transection requires primary anastamosis with catheter stinting, often resulting in severe scar formation and secondary bladder outlet obstruction. Balloon dilation (pressure balloon) to create new wound tissue may be performed or direct surgical resection removes the narrowed scar tissue. After one week, the original bladder catheter is exchanged for a silicone catheter coated with either BAPN-F or another lathyrogenic agent such as D-Penicillamine, which inhibits cross-linking (strong bonding) between scar collagen fibers. The coated catheter is continuously maintained in place and changed once a week for about six weeks during the healing phase. After catheter removal a normal sized opening is present, with the new scar being molded to the shape of the intraluminal stint (bladder urethral catheter.)

EXAMPLE 9 —URETHRA-PROSTATE RESECTION

Following partial prostatic resection for bladder neck obstruction in human males, approximately 10% of patients develop tubal narrowing at the origin of the urethra. The scar is resected to reopen the under direct surgical endoscopic vision. After one week, the lumen is protected with a catheter stint of silicone coated with a combination of D-Penicillamine and BAPN-F to inhibit cross-linking or hardening of the newly formed scar tissue. The catheter is continuously maintained in place and changed once a week for six weeks as healing is completed and new soft scar is layered around in the shape of the intraluminal stint. Once the stint is removed, the opening between the bladder and the beginning of the urethra is protected by the shape of the mature collagen scar which now progresses to slow cross-linking or hardening without narrowing the lumen.

EXAMPLE 10 —TRACHEA

The patient suffering tracheal injury either due to a tracheostomy on an emergency basis or secondary to an automobile accident has primary anastomosis of the trachea resulting in a severe scar and impairment of the airway. The scar is excised and an endotracheal silastic stint coated with 5.0 mM BAPN-F or D-Penicillamine is put in place after one week and continuously maintained and changed on a weekly basis for five or six weeks during the healing phase. The lathyrogen is incorporated in the newly formed and healing wound where it allows the newly formed scar to be soft, plastic-like and conform to the diameter of the endotracheal stint. Once healing is complete no further scarring takes place, the medication and stint is discontinued and the patient returns to normal airway dynamics.

EXAMPLE 11 —COMMON BILE DUCT STENOSIS

A patient who has had an injury of the common bile duct secondary to a complicated gallbladder operation is jaundiced. The scar is partially resected and after one week an original silastic stint is exchanged for an intraluminal silastic tube coated with BAPN-F with one arm of the tube protruding into the duodenum. The BAPN-F leaches off the silastic tube and is incorporated into the newly formed scar, which is soft because BAPN-F blocks cross-linking. The tube is continuously maintained in place and on a weekly basis the patient returns to the gastroenterology lab where, under direct manipulation, the tube is exchanged every week for six weeks. Once healing is complete the tube is removed and the new lumen of the common bile duct is preserved. The patient is no longer jaundiced and fluids from the liver can pass into the duodenum uninhibited.

In many of the foregoing examples it is beneficial to use a special catheter containing directly bonded BAPN-F. This provides the advantage that the BAPN-F will be delivered directly to the desired tissue without the danger of being partially or completely wiped off the catheter during insertion into the tubular organ.

Linking a drug such as BAPN-F to a polymer forming a catheter or wound dressing may be achieved by several methods including:

a. direct binding of the drug to available functional binding groups in the polymeric surface of the catheter;
b. linking the drug to newly created functional binding sites after chemical or physical modification of the polymeric surface;
c. direct incorporation of the drug into the polymeric surface either during the catheter manufacturing process or into the final catheter product by programmed, controlled soaking in the appropriate solution of the drug;
d. deposition of a drug in another polymeric substance (hydrogel, gelatin, collagen and the like) which is then chemically attached to the polymeric surface of the device. By this method large quantities of the drug can be associated with the effective surface of the device. The drug can be linked chemically to this coating material as well as physically sorbed if added in quantities exceeding the binding capacity of the coating polymer (hydrogel). An additional advantage of this process is that the coating polymer may add new properties to the device polymer, such as slipperiness, biocompatibility to tissue cells, reduction of mineral crystal formation when in contact with some biological fluids (urine).

Examples of manufacturing procedures for the above outlined processes are shown below:

A latex polymer may be partially hydrolyzed-depolymerized, for instance, in a strong oxidizing environment to provide free carboxyl, hydroxyl or amino groups when the polymer does not contain available functional groups. The groups then serve as sites for chemical binding of BAPN. In the case of BAPN binding, the availability of COO- groups is optional.

In practice, the latex polymer may be dipped into an aqueous solution of 2% sodium hypochlorite, wherein the solution contains 0.5% sulfuric acid. After 5–10 minutes of incubation at 25° C., the solution is decanted and the latex polymer incubated for another 5–10 minutes in 5% ammonium hydroxide solution. Removed polymer is then excessively washed in iced water. Activation of the COO- groups of the latex is achieved at 25oC in the presence of carbodiimide (10 mg/ml) at pH 4.75 of 0.1 M MES buffer. The incubation lasts 30 minutes, followed by quick ice water washing and then exposing the activated polymer to the solution of BAPN for 12 hours in 0.1 M MES at pH 4.75.

After completion of the reaction, the final product is not washed from the excess of the drug, which under these conditions contains both chemically and physically linked BAPN to the device polymer. In this medium, the carboxyl groups are activated and these react with the $\beta$-amino group of the BAPN-F to form a rather strong linkage. Carbodiimide having the chemical formula (1- ethyl-3 (3-dimethylamine-propyl) carbodiimide-HCl (EDC) has been recognized as a potent coupling agent activating the available carboxyl groups in hydrogel, collagen or gelatin.

When the device is made of inert or substantially inert silicones, known for their low polarity group content, the surface of the device may be modified to render more binding sites. The methods of modifying the silicone may be either chemical or physical. The example of using strong oxidizing agents was described above. Another method of forming reactive side groups in the silicone (activating the surface) is exposing a silicone surface to high energy ionizing radiation such as high energy electrons, X-ray or gamma radiation first and then interacting such a surface with BAPN-F under similar conditions as shown above. The radiation exposure total dose corresponds to 0.20 to 0.45 Merads. The principles of this method are the object of U.S. Pat. Nos. 3,453,194 or 3,826,678.

There is another method of bringing larger amounts of BAPN-F onto the surface of a polymer, such as latex or silicone. Either polymer is partially hydrolyzed as described above. To the activated surface of a polymer (a hydrogel, collagen or gelatin soluble in ethanol) is interacted to form a uniform coating. A reasonable amount of BAPN-F can be incorporated in such a coating of hydrogel, collagen or gelatin. The release of BAPN-F will then depend o the rate of diffusion of this molecule from the hydrogel, collagen or gelatin. This then will be controlled by the swellability of the hydrogel, collagen or gelatin. There are various types of hydrogels, based on polyacrylonitrile or polyurethanes, where hydration can vary from a few weight percent of water to almost 90% of water.

A purified collagen similar to hydrogels can be used to link with the functional groups of the polymer device, using known, described various procedures known in the art.

Selection of the appropriate hydrogel, collagen or gelatin will allow the desired release of BAPN-F. For instance, hydrogel based on polyurethane is available with free carboxyl groups (for example, see U.S. Pat. No. 4,255,550), lactone or hydroxyl groups (for example, see U.S. Pat. Nos. 4,156,066 and 4,156,067). In general, hydrophilic polymers or hydrogels are useful carriers for pharmaceutical agents (U.S. Pat. Nos. 3,975,350 or 4,439,585). Another factor controlling the rate of drug release from the hydrogel, collagen or gelatin coat (besides diffusibility) is the option of chemical binding of the drug to the functional (mainly carboxyl) groups of the hydrogel, collagen or gelatin.

It is known that lysyl oxidase, an enzyme essential for cross-linking of collagen (which results in strictures and contractures), is effectively, and irreversibly inhibited at $10^{16}$ M BAPN tissue concentration. Given that a) this concentration of BAPN, released every hour to reach a steady state in the tissue, is the safe and effective inhibitory dose and b) the treatment will last 10 days, the dose of BAPN deposited within the device to obtain zero order sustained release should exceed 24 mg of BAPN/device. In order to obtain zero order (linear) release of a drug from a matrix, it is important to combine at least two different mechanisms of a drug sorption (binding) in a polymer or matrix. These mechanisms include a) chemical binding of moderate strength providing slower release of a drug after its dissociation from the chemical bond and b) physical sorption, which is a very weak bond and allows immediate release of the drug once the device is exposed to tissue fluid and moisture. The kinetics of the release for each mechanism differ for various polymers and drugs.

One important factor favoring using hydrogels, collagens or gelatins as carrier for BAPN-F and other lathyrogenic substances is the similarity of hydrogel characteristics with tissue composition (same content of water, absence of toxic elements, similarity to collagen molecule chain in physical and physico-chemical aspects). Thus, hydrogel-drug implants or coatings of other polymer devices provides for better tissue tolerance.

Although several classes of hydrophilic polymers swellable in tissue fluids are available, the selection of the most appropriate hydrogel, collagen or gelatin is directed by criteria of safety, reflecting nontoxicity, noncarcinogenicity, mutagenicity, teratogenicity, etc. Furthermore, chemical reactions which lead to establishing a polymer (hydrogel)-drug complex, or which require additional cross-linking agents or activators, or which may cause difficulty in washing out the final product without compromising the stability of the linked drug, must be considered in the selection of an adequate coating polymer to be used as the reservoir for BAPN-F or other lathyrogen.

Other drug delivery systems for time release of lathyrogenic medications have been developed. Such delivery systems use biodegradable vehicles which are biologically safe, induce minimal local tissue reaction without any side toxic effects, are easy to handle, and are economically feasible.

For several years, gelatin-resorcinol-glutaraldehyde (G-R-Gl) tissue adhesive showed to be one of the least toxic tissue adhesives used in various surgical applications. The glue quickly polymerizes and efficiently adheres the tissue surfaces together when in contact with tissue and when reacted with formaldehyde or glutaraldehyde. The adhesive capacity depends on the content of R- which usually is 30% of total solids and on the concentration of the tanning agent used in the concentrated form. G-R-Gl as tissue adhesive has been applied to tissues in only minimal amounts, because the strength of the bonds is indirectly proportional to the thickness of the polymer in between the tissue surfaces.

Use of earlier tissue adhesive G-R-Gl polymers a vehicles for delivering lathyrogenic agents in the method of this invention is disadvantageous because the polymer consists of gelatin and resorcinol in weight ratio 3:1, G forms 33% and R forms 10% of the nonpolymerized solution. In other words, the original tissue adhesive mixture is a 60% aqueous solution consisting of 45 weight volumes of gelatin, 15 weight volumes of resorcinol and 40 volumes of water. After polymerization with 37% formaldehyde or 25% glutaraldehyde, a firm polymer is formed which undergoes, in biological environment, minimal swelling and slow resorption. High content of gelatin, resorcinol and tanning agent are essential to obtain solid tissue adhesion of high tensile strength. Thus, the lathyrogenic agent added to this earlier system would be released at an extremely slow rate.

We have found that by decreasing the content of the individual components and by varying the content of G, R and the concentration of tanning agent, mainly of Gl, it is possible to control the consistency and hydrophility of the final form of gel-polymer to release the lathyrogenic agent at a beneficial rate.

We have also found that if the lathyrogenic agent is added to the G-R-water mixture in appropriate concentration, then after quick mixing with selected concentrations of Gl in a syringe, the still fluid gel may be applied to the subject to form a polymer.

We have also found that in case faster drug release is desirable, R need not be present or added to the collagen solution during crosslinking by any tanning agent.

We found that a mixture consisting of 15 to 30 parts of G, 0.1–2 parts of R, 20 to 30 parts of water component and using 5 to 30 fold dilution of the Gl as polymerizing agent are optimal for long-term release of BAPN or other lathyrogenic agents over the period of several weeks or months.

A polymer consisting of only 1 to 5 parts of gelatin, 20 parts of water, of appropriate concentration of the lathyrogenic agent and polymerization induced by 0.05 ml of 0.5 to 3% glutaraldehyde per 1 milliliter of the mixture is optimal for short time release of the lathyrogenic agent over a period of a few weeks.

It was also found that the aqueous mixture consisting of collagen-resorcinol and the lathyrogenic agent can be coated on any biomaterial, prosthesis or device consisting of a biopolymer and then polymerized. After the plantation of the biomaterial on the healing wound a continuous release of the drug from the coat layer follows.

We have also found that when the lathyrogenic agent is added to the G-R mixture with another&her agent which has antithrombogenic properties such as heparin, a polymer can be coated on the healing biological tissue surface to prevent the formation of blood clots.

As indicated above, the rate of the release of the lathyrogenic agent depends on the degree of polymerization of the formed gel and also on the surface area of the polymer in contact with the healing wound. The rate of release of the lathyrogenic agent is controlled by the laws of physical diffusion as well a by the degree of biodegradability of the polymer. The rate of lathyrogenic agent diffusion then depends on the degree of hydration of the polymer.

The following examples serve to illustrate the practice of the invention, but are not to be regarded as limiting. All parts are given by weight, unless otherwise specified.

EXAMPLE 12

This example illustrates the efficacy of collagen-resorcinol-glutaraldehyde polymer as a BAPN-F delivery system. One hundred parts of medical grade purity collagen, prepared by a known procedure, is mixed with three hundred parts of water and heated until collagen dissolves to form a viscous solution. To this solution six parts of resorcinol are added and when this component dissolves, six parts of BAPN-F (Solution 1) or fifteen parts of BAPN-F (Solution 2) are mixed in. One milliliter of this mixture per kilogram of rabbit body weight was injected under the skin, after quick mixing of the appropriate volume of the mixture with 1/10 of its volume of 3 percent glutaraldehyde in a 5 ml plastic syringe. 1when this composite is injected under the skin, it polymerizes within a few minutes to form a pliable disk. The rate of the release of the BAPN-F from the polymer was studied by direct measuring of the amount of BAPN-F in the blood, collected from the ear vein of the rabbit at time intervals shown in Table 1.

For comparison, the same amount of BAPN-F was injected under the skin of control rabbits as water solution. It was found that while injection of the same amount of BAPN-F in water solution reaches a maximum in serum within two hours after injection, BAPN-F injected in the polymer mixture is released continuously and at a steady rate for seven days. Then its concentration in the blood slowly decreases.

TABLE 1

Release of BAPN-F From Two Polymer Mixtures as Compared With Water Solution of the Drug

| Time After the Injection (hrs) | Plasma Level[1] (BAPN-F) Water | Solution 1 | Solution 2 |
|---|---|---|---|
| 2 | 3.2 | 0.2 | 0.35 |
| 4 | 2.9 | 0.35 | 0.67 |
| 6 | 2.1 | 0.40 | 1.4 |
| 10 | 1.0 | 0.37 | 1.3 |
| 16 | 0.1 | 0.33 | 1.2 |
| 48 | 0 | 0.38 | 1.1 |
| 72 | 0 | 0.40 | 1.1 |
| 96 | 0 | 0.40 | 1.0 |
| 168 | 0 | 0.37 | 1.1 |

[1]BAPN-F was measured at given time intervals in the plasma of rabbits by a fluorometric method. Each point is the average of two determinations.

EXAMPLE 13

This example illustrates that the rate of the release of a drug from the polymer is controllable by changing the proportion of individual components of the mixture.

The mixture consisting of the above components, i.e. of collagen-resorcinol-water, was prepared in proportions given in Table 2.

TABLE 2

| Collagen | Water | Resorcinol | Plasma Level BAPN-F BAPN-F[1] (μg/ml) |
|---|---|---|---|
| 100 | 300 | 10 | 0.2 |
| 100 | 300 | 5 | 0.45 |
| 100 | 300 | 1 | 1.2 |

[1]Refers to values determined five days after injection of the delivery system with a drug.

6 parts of BAPN-F wee added to e ach type of mixture. One milliliter of each mixture per kilogram of rabbit body weight was injected and blood measurements were obtained as described in Example 12 The rate of release is shown in Table 2.

EXAMPLE 14 —PHYSICAL AND FUNCTIONAL STABILITY OF BAPN-F FILM

In order to demonstrate the functional stability of the BAPN-F film, a mixture of collagen-resorcinol-BAPN-F is prepared as follows: 10 g gelatin ar mixed with 31 ml water and heated on a water bath until a clear solution is formed. 3.3 g resorcinol are added and dissolved with stirring, and finally 200 mg BAPN-F are added to the solution. The mixture (1) remains liquid when kept at 40–50° C. A similar mixture (2) is prepared omitting BAPN-F. Two samples of a wet collagen membrane, containing 60% water by weight are coated on one side with a thin film of each mixture, the mixtures being kept at 50° C. when applied. When a homogenous film is obtained it is sprayed with 0.5% formaldehyde solution (concentrated HCHO 40%) and allowed to dry in 5 minute's. The excess of formaldehyde is washed out with water. The mixture is coated onto a plastic sheet at 50° C. When a continuous thin layer is formed the material is dipped into 2.0% glutaraldehyde solution for 1 second, and kept dry at 60° C until constant weight is reached. The net dry weight of the coating film is 320 mg. This film is removed from the plastic sheet and placed in an Erlenmeyer flask with 50 ml physiological saline solution and placed in a water bath fitted with a shaker. At time intervals as indicated in Table 3, samples were collected, hydrolyzed and analyzed for the presence of hydroxyprolines and hexosamines. The amount of hydroxyproline multiplied by 7.46 indicates the amount of dissolved collagen in mg, while the amount of hexosamines present multiplied by 3 indicates the amount of BAPN-F in solution. The ratio of solubility of collagen and BAPN-F was measured in saline at 37° C. in the incubation medium at periods during a 3 week interval. The dry weight of the incubated film totaled 335 mg.

The data in Table 3 shows that there is a negligible and proportional dissolution of both collagen and BAPN-F from the film into the 37° C. saline medium during extraction lasting almost 3 weeks, but that less than 5% collagen is dissolved, and no more than 2% BAPN-F.

TABLE 3

Physical and Functional Stability of Collagen-Resorcinol-BAPN-F-Glutaraldehyde Film in Saline at 37° C.

| Sampling Period (h) | Dissolved Collagen (mg) | % of Total Collagen in Film | Dissolved BAPN-F (μg) | % of Total BAPN-F in Film |
|---|---|---|---|---|
| 2 | 0.82 | 0.4 | 12 | 0.2 |
| 19 | 1.86 | 0.9 | 41 | 0.8 |
| 26 | 3.72 | 1.8 | 78 | 1.5 |
| 84 | 4.55 | 2.1 | 100 | 2.0 |
| 132 | 4.28 | 1.95 | 112 | 2.0 |
| 350 | 4.68 | 2.1 | 105 | 2.0 |
| 620 | 4.64 | 2.1 | 110 | 2.0 |

In order to obtain long shelf life of BAPN medications the drug should be kept dry and out of contact with water. For this reason administration of BAPN as an ointment, in gels or solutions is rather impractical, as the medication has to be freshly prepared every 6–8 weeks. 6–8 weeks is the time of detection of the first decomposition product of BAPN into ammonia, aminonitrile and $CO_2$. This invention can overcome the above problem by incorporating a solution with the known concentration of BAPN into the dressing material (gauze, collagen sponge) with a known surface area. The dressing material may be soaked with a known volume of BAPN solution, frozen and freeze dried to complete dryness. It has been established that at the dose of 20–40 mg BAPN-F per 100 $cm^2$ of the gauze there is an evident clinical effect of a topically applied gauze-placed wet over the lesions, such as peritendinous, perineural adhesions with prevention or reduction of the incidence of fibrotic adhesions.

Although this invention has been described in connection with specific forms thereof, it should be appreciated that a wide array of equivalents may be substituted for the specific elements shown and described herein without departing from the spirit and scope of this invention as described in the appended claims.

I claim:

1. A method of controlling scar formation in humans comprising:
 a) applying a force to tissue in an amount to create a wound;
 b) applying a lathyrogenic agent to the wound;
 c) forming the wound into a predetermined stationary or moveable beneficial configuration; and
 d) maintaining the wound in the predetermined configuration and in contact with lathyrogenic agent during healing.

2. The method defined in claim 1 wherein the tissue is scar tissue.

3. The method defined in claim 1 wherein the tissue is substantially tubularly shaped.

4. The method defined in claim 3 wherein the substantially tubularly shaped tissue is selected from the group consisting of urethra, esophagus, intestine, fallopian tubes and blood vessels.

5. The method defined in claim 1 wherein the lathyrogenic agent is B-aminopropionitrile fumarate.

6. The method defined in claim 3 wherein the step of applying the lathyrogenic agent includes the step of placing the lathyrogenic agent on a catheter and inserting the catheter into the tubularly shaped tissue to a point where the lathyrogenic agent directly and closely contacts the wound.

7. The method defined in claim 6 wherein the lathyrogenic agent is ionically bonded to an outer portion of the catheter.

8. The method defined in claim 3 wherein the step of applying force to the tissue includes expanding a balloon catheter against the tissue.

9. The method defined in claim 3 wherein the step of applying force to the tissue includes inserting a tube into the tissue having a diameter greater than that of the tubular tissue.

10. The method defined in claim 3 wherein the tissue is maintained in a forced condition by an expanded balloon catheter.

11. The method defined in claim 3 wherein the tissue is maintained in a forced condition by a tube having a diameter greater than that of the tubular tissue.

12. A method of treating tubular organ stenosis in humans comprising:
 a) forcefully stretching a fibrotic lesion located inside a tubular shaped human body portion to tear existing scar tissue in the lesion and create a new wound;
 b) applying B-aminopropionitrile fumarate onto a catheter;
 c) inserting the catheter into the tubular body portion for a distance to cause B-aminopropionitrile fumarate/wound contact, thereby initiating softening of the wound; and
 d) retaining the catheter in place to continuously maintain the wound in a stretched condition so that the body portion will substantially retain the size of the catheter.

13. A method of reshaping scar tissue in humans comprising:
 a) stretching scar tissue in an amount to increase flexibility and lengthen or expand the tissue by exposing normal tissue;
 b) holding the flexible scar tissue in a desired shape;
 c) applying a lathyrogenic agent to the flexible scar tissue to soften the healing tissue; and
 d) simultaneously, maintaining the softened, flexible scar tissue in the desired shape during healing.

14. The method defined in claim 1 wherein the lathyrogenic agent is contained in a heat denatured collagen-resorcinol-water solution as a vehicle, the mixture is polymerized for releasing slowly and continuously the lathyrogenic agent, thus forming a drug delivery system.

15. The method of claim 14 wherein the solution comprises about 10 to 30 parts of collagen or gelatin, about 1 to 0.1 parts of resorcinol and about 20 to 40 parts of water.

16. The method of claim 14 wherein the heat denatured collagen solution is polymerized in the presence of a tanning agent.

17. The method defined in claim 16 including the steps of coating the collagen mixture with the lathyrogenic agent and polymerizing it on the surface of the wound.

18. The method defined in claim 1 using a scar inhibiting composition adapted for application to the biological surface, said scar inhibiting composition comprising a lathyrogenic agent and a condensation product of a high molecular weight protein and a dihydric phenol, said condensation product being crosslinked with a biologically nontoxic tanning agent.

19. The method defined in claim 17 wherein the collagen mixture is in the form of an aerosol spray solution.

20. The method defined in claim 1 wherein the lathrogenic agent is incorporated into a cream or gauze bandage applied to the skin surface at a concentration of about 40 mg BAPN/100 $cm^2$ skin area.

21. A method of controlling scar formation in humans comprising:

a. applying a force to substantially tubularly shaped tissue in an amount to create a wound, wherein the tissue is selected from the group consisting of urethra, esophagus, intestine, fallopian tubes and blood vessels;
b. applying a lathyrogenic agent to the wound;
c. forming the wound into a predetermined beneficial configuration; and
d. maintaining the wound in a predetermined configuration and in contact with lathyrogenic agent during healing.

22. A method of controlling scar formation in humans comprising:

a. applying a force to substantially tubularly-shaped tissue in an amount to create a wound;
b. applying a lathyrogenic agent to the wound, wherein the lathyrogenic agent is placed on a catheter and the catheter is inserted into the tubularly-shaped tissue to a point where the lathyrogenic agent directly and closely contacts the wound;
c. forming the wound into a predetermined beneficial configuration; and
d. maintaining the wound in a predetermined configuration and in contact with lathyrogenic agent during healing.

23. The method defined in claim 22 wherein the lathyrogenic agent is ionically bonded to an outer portion of the catheter.

24. A method of controlling scar formation in humans comprising:

a. applying a force to substantially tubularly shaped tissue in an amount to create a wound;
b. applying a lathyrogenic agent to the wound;
c. forming the wound into a predetermined beneficial configuration; and
d. maintaining the wound in a predetermined configuration and in contact with lathyrogenic agent during healing.

25. The method defined in claim 24 wherein the step of applying force to the tissue includes expanding a balloon catheter against the tissue.

26. The method defined in claim 24 wherein the step applying force to the tissue includes inserting a tube into the tissue having a diameter greater than that of the tubular tissue.

27. The method defined in claim 24 wherein the tissue is maintained in a forced condition by an expanded balloon catheter.

28. The method defined in claim 24 wherein the tissue is maintained in a forced condition by a tube having a diameter greater than that of the tubular tissue.

* * * * *